(12) United States Patent
Campbell et al.

(10) Patent No.: US 10,596,263 B2
(45) Date of Patent: *Mar. 24, 2020

(54) PAZOPANIB FORMULATION

(71) Applicant: Novartis AG, Basel (CH)

(72) Inventors: Gossett Augustus Campbell, Collegeville, PA (US); Helen Richardson, Wales (GB); Peter A. Williams, Wales (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,143

(22) Filed: Aug. 22, 2018

(65) Prior Publication Data

US 2018/0360971 A1    Dec. 20, 2018

Related U.S. Application Data

(63) Continuation of application No. 14/994,497, filed on Jan. 13, 2016, now Pat. No. 10,080,802, which is a continuation of application No. 14/353,141, filed as application No. PCT/US2012/060361 on Oct. 16, 2012, now Pat. No. 9,278,099.

(Continued)

(51) Int. Cl.
| | |
|---|---|
| *A61K 47/36* | (2006.01) |
| *A61K 47/32* | (2006.01) |
| *A61K 47/38* | (2006.01) |
| *A61K 47/46* | (2006.01) |
| *A61K 31/506* | (2006.01) |
| *A61K 9/00* | (2006.01) |

(Continued)

(52) U.S. Cl.
CPC ............ *A61K 47/36* (2013.01); *A61K 9/0095* (2013.01); *A61K 9/14* (2013.01); *A61K 9/1623* (2013.01); *A61K 9/1652* (2013.01); *A61K 31/506* (2013.01); *A61K 47/32* (2013.01); *A61K 47/38* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 2007/0292513 | A1 | 12/2007 | Booloor et al. |
| 2009/0005406 | A1 | 1/2009 | Pandite et al. |

(Continued)

FOREIGN PATENT DOCUMENTS

| | | |
|---|---|---|
| CA | 2002472 A1 | 5/1990 |
| GB | 2217598 A1 | 3/1989 |

(Continued)

OTHER PUBLICATIONS

Heath et al., "A phase I pharmacokinetic and safety evaluation of oral pazopanib dosing administered as crushed tablet or oral suspension in patients with advanced solid tumors", Investigational New Drugs, Journal of New Anticancer Agents, 2012, vol. 30, No. 4, pp. 1566-1574.

(Continued)

*Primary Examiner* — Bethany P Barham
*Assistant Examiner* — Barbara S Frazier
(74) *Attorney, Agent, or Firm* — Michelle Han

(57) ABSTRACT

A granulation formulation of 5-[[4-[(2,3-dimethyl-2H-indazol-6-yl)methylamino]-2-pyrimidinyl]amino]-2-methylbenzenesulfonamide or pharmaceutically acceptable salt thereof, which is adapted for reconstitution with an aqueous vehicle, and associated oral suspension.

6 Claims, 2 Drawing Sheets pH solubility profile

Related U.S. Application Data

(60) Provisional application No. 61/553,454, filed on Oct. 31, 2011.

(51) Int. Cl.
  *A61K 9/14* (2006.01)
  *A61K 9/16* (2006.01)

(56) References Cited

U.S. PATENT DOCUMENTS

| | | |
|---|---|---|
| 2009/0137580 A1 | 5/2009 | Imamura et al. |
| 2009/0258069 A1 | 10/2009 | Burnier et al. |
| 2010/0221247 A1 | 9/2010 | Bender et al. |
| 2010/0267787 A1 | 10/2010 | Harasymiw et al. |
| 2010/0291025 A1 | 11/2010 | Rao et al. |
| 2012/0015990 A1 | 1/2012 | Hsieh et al. |

FOREIGN PATENT DOCUMENTS

| | | |
|---|---|---|
| RU | 2241460 C2 | 12/2004 |
| RU | 2003130115 A | 4/2005 |
| RU | 2381223 | 2/2010 |
| WO | 2007/064752 A2 | 6/2007 |
| WO | 2007/089445 A2 | 8/2007 |
| WO | WO2009098649 A1 | 8/2009 |
| WO | 2011024122 A1 | 3/2011 |

OTHER PUBLICATIONS

Lee et al., "Thixotropic property in pharmaceutical formulations", Journal of Controlled Release, 2009, vol. 136, pp. 88-98.
European Medicines Agency, "CHMP assessment report: Votrient", pp. 1, 5, 6 (2010).
Ursino et al., "Excipients in medicinal products used in gastroenterology as a possible cause of side effects", Regulartory Toxicology and Pharmacology, 2011, vol. 60, pp. 93-105.
ORA-SWEET Flavored Syrup Vehicle, 2010.
Remington et. al.,"Remington: the science and practice of pharmacy", 2000, 10th edition, p. 321, 2000.

Effects of PVP on the viscosity of suspension pH solubility profile

PAZOPANIB FORMULATION

FIELD OF THE INVENTION

The present invention relates to pharmaceutical compositions containing, as an active ingredient, 5-[[4-[(2,3-dimethyl-2H-indazol-6-yl)methylamino]-2-pyrimidinyl]amino]-2-methylbenzenesulfonamide as well as use of the compositions in the treatment of proliferative diseases such as cancer. In particular, the pharmaceutical compositions contain 5-[[4-[(2,3-dimethyl-2H-indazol-6-yl)methylamino]-2-pyrimidinyl]amino]-2-methylbenzenesulfonamide as an active ingredient that is an inhibitor of VEGF.

BACKGROUND OF THE INVENTION

Pazopanib is an angiogenesis inhibitor targeting vascular endothelial growth factor receptors (VEGFR)-1, -2, and -3, platelet-derived growth factor receptors (PDGFR)-α/-β, and c-Kit. The hydrochloride salt of pazopanib (5-[[4-[(2,3-dimethyl-2H-indazol-6-yl)methylamino]-2-pyrimidinyl]amino]-2-methylbenzenesulfonamide) is marketed by GlaxoSmithKline as Votrient®, which is approved in the United States and other countries for the treatment of renal cell carcinoma (RCC).

Votrient® is currently prescribed to adults in the form of 200 mg tablets for oral administration, with each 200 mg tablet containing an amount of pazopanib hydrochloride equivalent to 200 mg of pazopanib free base.

Though the current tablets are acceptable of use in adults, the tablets are not preferred for use in potential future use for administering pazopanib to children. In pediatric populations, it is often desired that drug be available as a powder for reconstitution to an oral suspension. Manufacture of such a powder requires dry blending of various excipients with the active substance to provide good flow properties and content uniformity of the powder blend.

Several additional challenges exist concerning the use of pazopanib in a pediatric formulation. For instance, the nature of the drug substance favors conversion from the hydrochloride salt to the free base and hydrate forms in an aqueous environment such that standard formulations fail to provide adequate suspension stability at long term storage conditions of 25° C./65% RH or room temperature. Further, the drug has been found to have a bitter taste and, therefore, taste masking is critical.

It is desired to invent a pediatric formulation of pazopanib hydrochloride suitable for administration to a pediatric population.

SUMMARY OF THE INVENTION

The present invention is related to a direct blend formulation of 5-[[4-[(2,3-dimethyl-2H-indazol-6-yl)methylamino]-2-pyrimidinyl]amino]-2-methylbenzenesulfonamide or pharmaceutically acceptable salt thereof, which is adapted for reconstitution with an aqueous vehicle. This invention is also related to a prepared aqueous suspension, or dispersion, formulation, particularly to a stable oral pharmaceutical formulation, comprising 5-[[4-[(2,3-dimethyl-2H-indazol-6-yl)methylamino]-2-pyrimidinyl]amino]-2-methylbenzenesulfonamide or pharmaceutically acceptable salt thereof mixed with an aqueous vehicle. Additionally, the present invention is related to the method of preparing these formulations.

DETAILED DESCRIPTION

Figure 1:
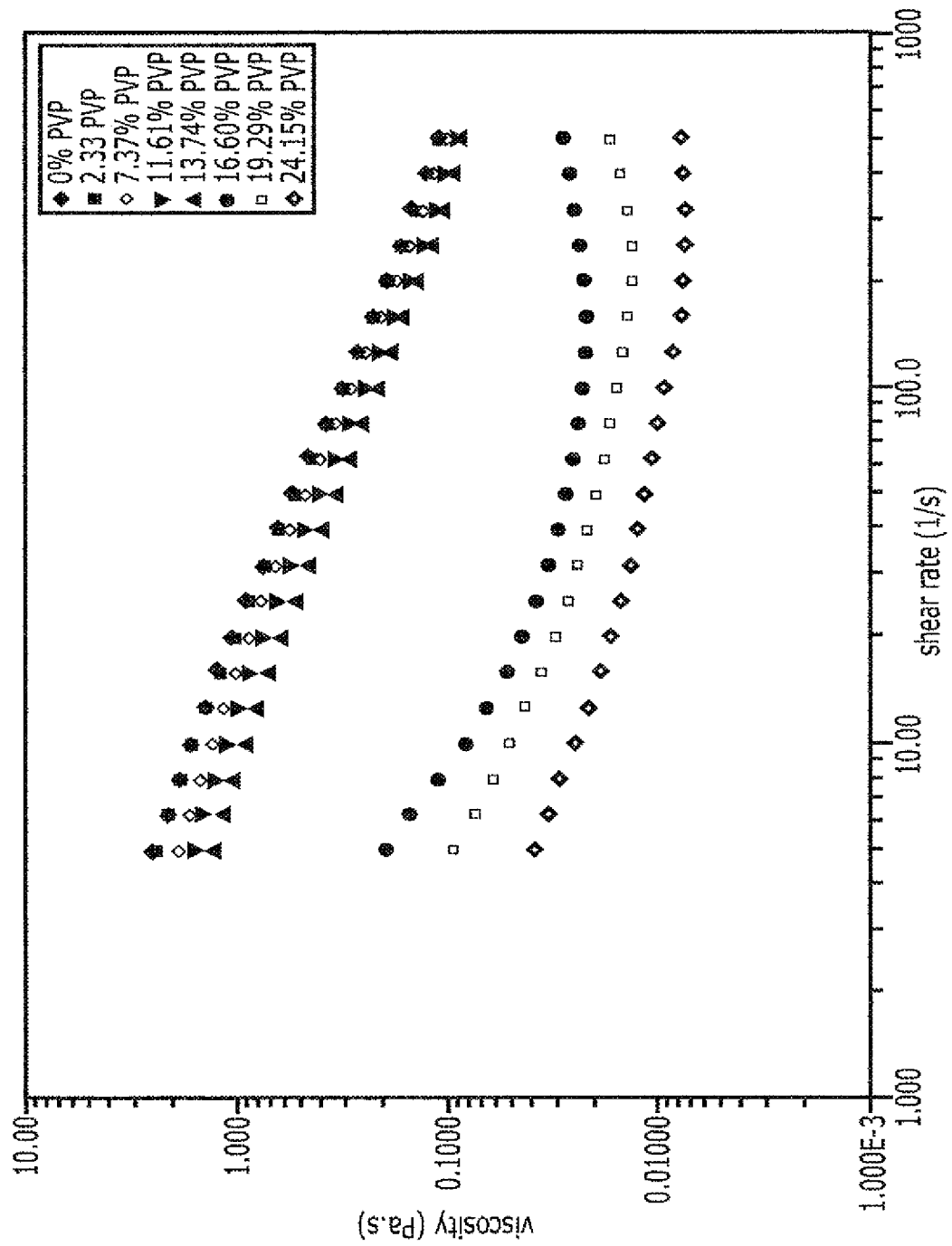
FIG. 1 is a graph showing the effect of PVP content on the viscosity of the disclosed formulation.

According to one embodiment, the present invention is a direct powder blend formulation of 5-[[4-[(2,3-dimethyl-2H-indazol-6-yl)methylamino]-2-pyrimidinyl]amino]-2-methylbenzenesulfonamide or pharmaceutically acceptable salt thereof, which is adapted for reconstitution with an aqueous vehicle.

According to another embodiment, there is provided a direct powder blend formulation comprising 5-[[4-[(2,3-dimethyl-2H-indazol-6-yl)methylamino]-2-pyrimidinyl]amino]-2-methylbenzenesulfonamide or pharmaceutically acceptable salt thereof, thickening agent, suspending agent, buffer, and sweetener.

According to another embodiment, there is provided a direct powder blend formulation comprising 5-[[4-[(2,3-dimethyl-2H-indazol-6-yl)methylamino]-2-pyrimidinyl]amino]-2-methylbenzenesulfonamide hydrochloride, thickening agent, suspending agent, buffer, and sweetener.

According to another embodiment, there is provided a direct powder blend formulation comprising micronized 5-[[4-[(2,3-dimethyl-2H-indazol-6-yl)methylamino]-2-pyrimidinyl]amino]-2-methylbenzenesulfonamide hydrochloride, thickening agent, suspending agent, surfactant, buffer, preservative, anti-adherent, sweetener, and flavor.

According to another embodiment, there is provided a direct powder blend formulation comprising micronized 5-[[4-[(2,3-dimethyl-2H-indazol-6-yl)methylamino]-2-pyrimidinyl]amino]-2-methylbenzenesulfonamide hydrochloride, guar gum as a thickening agent, polyvinylpyrrolidone (PVP) as a suspending agent, Polysorbate 80 as a surfactant, citric acid and sodium phosphate as buffers, methylparaben as an antimicrobial preservative, colloidal silicon dioxide as an anti-adherent, sucralose and mannitol as a sweetener, and lemon flavor.

According to another embodiment, there is provided a direct powder blend formulation comprising 35.0 to 50.0 w/w % micronized 5-[[4-[(2,3-dimethyl-2H-indazol-6-yl)methylamino]-2-pyrimidinyl]amino]-2-methylbenzenesulfonamide hydrochloride, 3.0 to 8.0 w/w % guar gum as a thickening agent, 3.0 to 12.0 w/w % (or advantageously 3.2 to 7.8 w/w %) polyvinylpyrrolidone (PVP) as a suspending agent, 0.02 to 0.55 w/w % Polysorbate 80 as a surfactant, about 4.7 w/w % citric acid and about 4.0 w/w % sodium phosphate as buffers, 1.2 to 2.0 w/w % methylparaben as an antimicrobial preservative, 0.32 to 0.64 w/w % colloidal silicon dioxide as an anti-adherent, 5.0 to 11.0 w/w % sucralose and 18.0 to 30.0 mannitol as a sweetener, and 1.0 to 5.0 w/w % lemon flavor.

According to another embodiment, there is provided an oral suspension comprising 5-[[4-[(2,3-dimethyl-2H-indazol-6-yl)methylamino]-2-pyrimidinyl]amino]-2-methylbenzenesulfonamide hydrochloride, thickening agent, suspending agent, surfactant, buffer, preservative, anti-adherent, sweetener, flavor, and an aqueous vehicle.

According to another embodiment, there is provided an oral suspension comprising 5-[[4-[(2,3-dimethyl-2H-indazol-6-yl)methylamino]-2-pyrimidinyl]amino]-2-methylbenzenesulfonamide hydrochloride, guar gum as a thickening agent, polyvinylpyrrolidone (PVP) as a suspending agent, Polysorbate 80 as a surfactant, citric acid and sodium phosphate as buffers, methylparaben as an antimicrobial preservative, colloidal silicon dioxide as an anti-adherent, sucralose and mannitol as a sweetener, lemon flavor, and water.

The components of the direct powder blend may be combined in any order, either individually or with two or more components of the blend being pre-mixed. According to one embodiment, guar gum, mannitol and polysorbate 80 are combined into a single multi-component granules prior to combination with the other ingredients.

Pazopanib, which is preferably present as a monohydrochloride salt, is 5-[[4-[(2,3-dimethyl-2H-indazol-6-yl)methylamino]-2-pyrimidinyl]amino]-2-methylbenzenesulfonamide, shown below as formula (I):

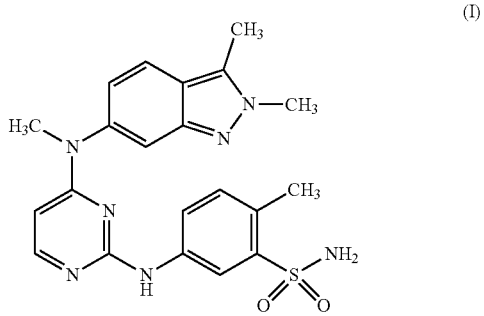 [SMILES: Cc1ccc(Nc2nccc(N(C)c3ccc4c(C)n(C)nc4c3)n2)cc1S(N)(=O)=O]

Pazopanib is disclosed and claimed, along with pharmaceutically acceptable salts thereof, as being useful as an inhibitor of VEGFR activity, particularly in treatment of cancer, in international Application No. PCT/US01/49367, having an International filing date of Dec. 19, 2001, International Publication Number WO02/059110 and an International Publication date of Aug. 1, 2002, the entire disclosure of which is hereby incorporated by reference. Pazopanib can be prepared as directed in the WO'110 publication. Particularly, the monohydrochloride salt of pazopanib is described in Example 69.

The pazopanib active substance is preferably micronized. Micronization of the pazopanib has been found to enhance the solubility and in-vivo exposure of the drug. Particle size reduction also helps to improve the mouth-feel of the suspension. Micronization may be achieved using techniques known in the art. According to one embodiment, particle size reduction is achieved through the use of fluid energy jet mill wherein the powder gets suspended in a high velocity nitrogen gas stream in a milling chamber, and particle size is reduced due to the principle of impact and attrition due to the high velocity collisions between particles suspended within the nitrogen gas stream, causing them to break down into smaller particles. Centrifugal force causes the larger, heavy particles to separate from smaller, lighter particles. The small particles are dragged by the escaping fluid stream towards the center of the mill, where they are discharged into filter bags, and the material is then collected into drums. The large particles are thrown outward where they recirculate and re-collide, causing them to breakdown. According to one embodiment, the resulting particle size distribution of pazopanib hydrochloride particles is >90% between 0.61 and 10.0 microns. In another embodiment, at least 50% is from 1 to 10 microns, preferably from 1.1 to 3.9 microns. In another embodiment 90% is 20 microns or less, preferably 10 microns or less.

The micronized pazopanib is advantageously present in the direct blend powder formulation (before reconstitution in aqueous vehicle) in an amount from about 35% to about 50% w/w, and further alternatively between 35% and 45% w/w. According to another embodiment, the amount of micronized pazopanib is about 39.0% to 41.6% w/w.

Examples of the thickening agent, suspending agents, surfactants, buffers, preservatives, sweeteners, and flavors are understood in the art, such components are described, for example, in Martindale—The Extra Pharmacopoeia Pharmaceutical Press, London (1993) and Martin (ed.), Remington's Pharmaceutical Sciences.

According to one embodiment, "thickening agent" is a substance (liquid or solid) which increase the viscosity of a solution, suspension, or liquid/solid mixture without substantially modifying its other properties. Thickeners may also improve the dispersion of other ingredients or emulsions which increases the stability of the product. Some also proves thixotropic properties, shear dependent viscosity, for example Guar gum. For instance, suitable thickening agents include, but are not limited to, protective colloids or non-ionic gums such as hydroxyethylcellulose, hydroxypropylcellulose, xanthan gum, guar gum, magnesium aluminum silicate, silica, microcrystalline wax, beeswax, paraffin, and cetyl palmitate. Preferred thickening agents are xanthan gum and guar gum. Guar gum is more preferred.

According to one embodiment, "suspending agent" is a substance (liquid or solid) that helps to keep the drug uniformly dispersed or suspended in a suspension. A suspending agent reduces or eliminates the sedimentation rate of particles in suspension. For instance, suitable suspending agents include, but are not limited to, hypromellose, polyvinylpyrrolidone, and commercially available suspending agents such as Avicel® RC-591, Avicel® CL-611, and SEPITRAP®. PVP is most preferred but the amount of PVP is also important as is explained below.

According to one embodiment, "viscosity modifier" is a substance (liquid or solid) that reduces the change in viscosity due to changes in temperature.

According to one embodiment, "surfactant" is a surface active agent that lowers the surface tension of a liquid, the interfacial tension between two liquids, and the interfacial tension between a liquid and a solid, thereby increasing the wettability of the drug particles in suspension. For instance, suitable surfactants include, but are not limited to, Hypromellose (HPMC), Polysorbate 80, Polysorbate 20, and Sodium Lauryl Sulphate (SLS).

As used herein, "buffer" is a mixture of a weak acid and its conjugate base or a weak base and its conjugate acid that is used to resist the change in pH by the addition of a small amount of acid or base.

As used herein, "preservative" is used to prevent the growth of bacteria and/or fungi in the liquid formulation. For instance, suitable preservatives include, but are not limited to, parabens (methyl, ethyl, propyl, and butyl), paraben sodium salt, potassium sorbate, sodium benzoate, and sorbic acid.

As used herein, "anti-adherent" or "glidant" are used alternatively to improve the flowability of the powder and reduce sticking of the suspended particle to inner walls of the container.

As used herein, "sweetener" is a substance (solid or liquid) that is used to improve the palatability of the formulation. For instance, suitable sweeteners include, but are not limited to xylitab, xylitol, mannitol, sucrose, sucralose, saccharin, ammonium and sodium glyceryrhizinate, aspartame, and sorbitol.

According to one embodiment, "process aid" is a substance (solid or liquid) used to enhance the processibility of the formulation. For example, if the drug adheres to the walls of the blender the use of a granular excipient such mannitol can remove the drug off the walls of the blender and help to disperse the drug uniformly.

As used herein, "flavor" is a substance (liquid or solid) that provides a distinct taste and aroma to the formulation. Flavors also help to improve the palatability of the formulation.

As used herein, "vehicle" is a liquid use to reconstitute a powder into an oral suspension or solution. The vehicle needs to be compatible with the formulation so that stability can be attained and maintained. For instance, suitable vehicles include, but are not limited to, purified water, sterile water for injection, sterile water for irrigation, Ora-Sweet®, Ora-Plus®, and Pro-Sweet®. According to one embodiment, the vehicle is purified or sterile water.

Concerning viscosity, early attempts to formulate the composition of the invention into an oral suspension caused difficulty. Several commercially available suspension vehicles were tried, and each resulted in a very thick suspension, phase separation or settling, solidification, or gellation. For instance, various mixtures of each of purified water, Suspendol®, Ora-Sweet®, and Ora-Plus® Syrup vehicles failed to be satisfactory. Only a formulation that was reconstituted with 3:1 v/v ratio of Ora-Sweet® syrup and purified water was exceptionally stable by XRPD, based on physical stability for 35 days at 25° C./60% RH and room temperature. Although this formulation was found to be acceptable for clinical use, the suspension became very thick and lumpy overtime, which caused problems in dispensing and dosing, the agglomeration resulted in settling. In addition, the suspension tends to build up and cake on the inner walls on the container.

The inventors discovered that Guar gum gives the invented suspension thixotropic properties that allow the suspension viscosity to decrease as the container is shaken for ease of pouring or dispensing and administration of accurate doses. As the container remains undisturbed the viscosity of the suspension increases causing the active particles to remain suspended, which eliminates settling, and agglomeration/lumping. Guar gum is preferably present in the compositions of the invention as 3 to 12% by weight, more preferably from 4 to 9% by weight.

The use of PVP in the suspension as a viscosity modifier further enhances the stability of the suspension under long term storage. It was observed that the viscosity of the suspension decreased with an increase in the amount of PVP. In FIG. 1 the effect of PVP on the viscosity of the suspension is demonstrated. For instance, at PVP levels above about 13% the suspension viscosity decreases significantly and resulted in shorter physical stability under long term storage conditions. The optimum PVP concentration was determined to be around 7% w/w of powder. Preferably, the compositions of this invention contain PVP as from 2 to 14% by weight, more preferably from 7 to 14% by weight. This effect of decrease in viscosity with increase in PVP amount is most likely due to the faster hydration rate of PVP compared to gaur gum. While not wanting to be bound by a particular theory, it may be that upon dilution or reconstitution, the PVP is preferentially hydrated resulting in an incomplete hydration of gaur gum, which causes the viscosity to decrease.

Thus, the use of PVP at levels specified herein enhances the physical stability of the suspension, and the use of guar gum and PVP in the formulation allows reconstitution with purified water with significant increase in physical stability compared to suspensions prepared according to standard practice.

Regarding the use of buffers, physical stability of the invented suspension was determined to be a function of pH, temperature, buffering system, and buffer strength as shown in Table I (some repeat runs are shown).

TABLE 1

| Buffer System | Buffer strength | Initial pH | PVP [% wt/wt] | Physical Stability @ 5° C./Ambient | Physical Stability @ 25° C./60% RH |
|---|---|---|---|---|---|
| Citric Acid/ Sodium Citrate | 0.2M | 4.0 | 0 | Mixture by day 21; Conversion to Citrate salt by day 42 | Conversion to Citrate salt by day 7 |
| Citric Acid/ Sodium Citrate | 0.5M | 4.0 | 0 | Conversion to Citrate salt by day 14 | Mixture at initial; Conversion to Citrate salt by day 14 |
| Citric Acid/ Sodium Phosphate | 0.2M | 4.0 | 0 | 43 days | At least 7 Days; Conversion to Citrate salt by day 20 |
| Citric Acid/ Sodium Phosphate | 0.1M | 4.0 | 0 | 43 days | At least 7 Days; Mixture of forms by day 20 |
| Citric Acid/ Sodium Phosphate | 0.05M | 4.0 | 0 | 43 days | At least 7 Days; Mixture of forms by day 20 |
| Citric Acid/ Sodium Citrate | 0.05M | 4.0 | 0 | 43 days | Mixture of forms by day 7 |
| Citric Acid/ Sodium Phosphate | 0.2M | 3.5 | 0 | Conversion to Citrate salt by day 17 | n/a |
| Citric Acid/ Sodium Phosphate | 0.2M | 3.2 | 0 | Conversion to Citrate salt by day 17 | n/a |
| Citric Acid/ Sodium Phosphate | 0.2M | 3.0 | 0 | Conversion to Citrate salt by day 17 | n/a |

Conversion of pazopanib to the citrate salt in citric acid and sodium citrate buffer system at pH 4.0 and buffer strength of 0.05 M to 0.5 M was observed at initial to day 7 when stored at long term storage conditions of 25° C./60% RH and at 5° C. form conversion started at least on day 14. By removing the sodium citrate from the buffering system the rate of formation of the citrate salt under both refrigerated and long term storage conditions was impeded. Suspensions containing citric acid and sodium phosphate buffering system at pH 4.0 with buffer strength from 0.05 to 0.20 M and no PVP were all stable up to 43 days at refrigerated conditions. At long term storage conditions of 25° C./60% RH form conversion was detected at day 7 but the citrate salt was first observed on day 20.

The addition of PVP to the suspension buffered with citric acid and sodium phosphate at pH 4.0 and buffering strength 0.05 M increases the physical stability to at least 20 days. At PVP levels between 3.8 to 7.4% w/w, inclusive, the pazopanib monohydrochloride salt was maintained until 34 days.

Figure 2:
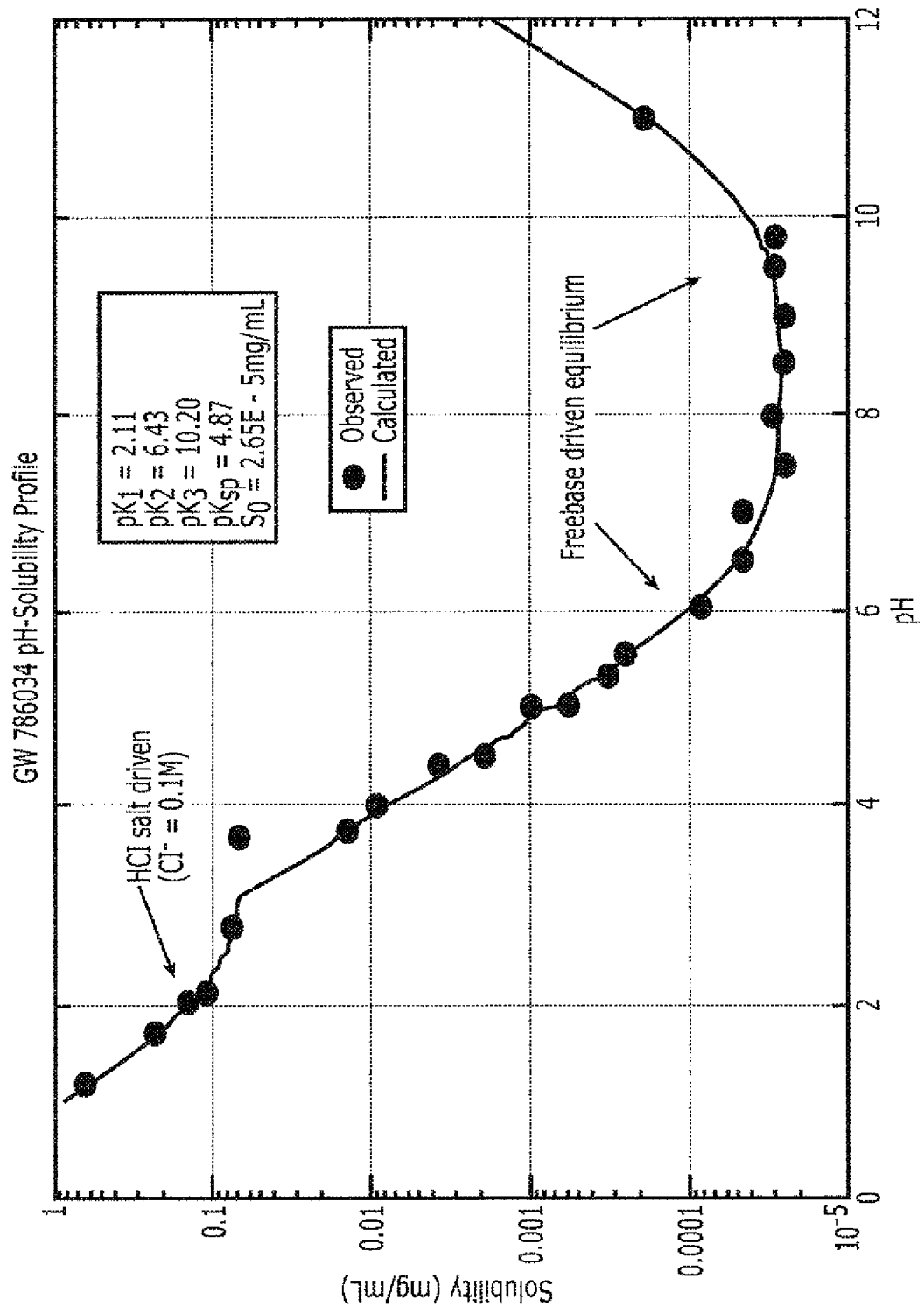
FIG. 2 is a graph showing the solubility of pazopanib in water at various pH.

Based on the pH-solubility curve of pazopanib (FIG. 2) the solubility profile between pH 3 and pH 6 is on a steep slope and therefore, small changes in pH will have a large change in solubility. At the lower pH levels the citrate and monohydrate salts predominate and at the higher pH the freebase predominates. When the suspension is buffered at pH 3.5 and below with citric acid and sodium phosphate buffering system, the drug substance in the suspension changes form to the hydrate and Citrate salts in less than 17 days after reconstitution under refrigerated storage condition 5° C. This indicates that the physical stability of pazopanib is better controlled around a pH of 4. Therefore, the compositions of this invention are such that when reconstituted they preferably provide a suspension with a pH from 2.5 to 4.5, preferably a pH of from 3.0 to 4.2, and most preferably a pH of from 3.5 to 4.0.

The taste of previous formulations of pazopanib has been summarized as being bitter with a gritty mouth feel. The taste perception of the suspension formulation was assessed by the Astree® electronic tongue (e-tongue). The e-tongue measures and maps the relative repartition and proximity of the taste between an active suspension formulation and its matching placebo. The e-tongue measurements are analyzed by principal component analysis (PCA). It is assumed that the placebo represents the ideal "target" taste profile, since the bitter active component is not present. Therefore, masking of bitterness or taste proximity is quantified using the euclidean distance between the active and placebo formulations on the PCA map, with a smaller distance indicating a flavor that is doing a better job of masking and therefore bringing the active and placebo e-Tongue "fingerprint" closer together. The discrimination index (Dl in %) takes into account the difference between the center of gravity of the sensors output for each pair of formulation as well as the dispersion within the sensors output for the formulations. The higher the value of discrimination index (closer to 100%), the less similarity between the formulations and less masking occurred.

Multiple different flavors and combinations were tested at 0.3% in the suspension formulation and its matching placebo to assess their masking efficiency. Not all the flavors decreased the distance of the unmasked pazopanib suspension. For example, after adding Grape or Vanilla to the base suspension, the distance increases suggesting less similarity in taste perception between the unflavored and flavored suspensions. All the other flavors when added to the base suspension decreased the distance. However, the discrimination indices indicated that the tested lemon and cherry flavorings were the most effective in masking the bitter taste of pazopanib suspension. This result was in concordance with a human taste panel and therefore, lemon flavor was selected as a preferred flavor, along with sweeteners for taste, preferably sucralose and mannitol.

Mannitol is also used to provide good processability of the powder by enhancing the flow properties and content uniformity of the powder blend. In addition to the above excipients, a surfactant and/or anti-adherent may be used to aid in the wetting of the active substance and preventing sticking/caking of the suspension to the inner wall of the container.

In addition to the above excipients, a surfactant and/or anti-adherent may be used to aid with good flow properties and content uniformity of the powder blend, both during powder manufacture and storage.

Antimicrobial or other preservatives may be added to extend in use longevity. An exemplary antimicrobial is methylparaben.

EXAMPLES

As used herein the symbols and conventions used in these processes, schemes and examples are consistent with those used in the contemporary scientific literature, for example, the Journal of the American Chemical Society or the Journal of Biological Chemistry. Unless otherwise indicated, all temperatures are expressed in ° C. (degrees Centigrade). All reactions conducted under an inert atmosphere at room temperature unless otherwise noted.

Example 1

Preparation Exemplary Formulation
(i) Formation of Single Multi-Component Placebo Granules (Batch Size—110 Kilograms)

To provide adequate secondary processability of the formulation a spray dried granulation of Guar gum, Mannitol and Polysorbate 80 was manufactured in a Glatt WST60 250 L bowl granulator using fluidized air technology. The Mannitol (66% w/w) and Guar gum (29.9% w/w) powder were added to the granulator. A solution containing 14% of polysorbate 80 (amount of polysorbate 80 added is 4% w/w of batch size) and 0.3% of Guar gum (amount of Guar gum added is 0.1% w/w of batch size) in water was prepared using a lightnin' mixer in a suitable size container. The mannitol and guar gum in the Glatt 250 L bowl were fluidized and pre-heated using an inlet air temperature of 80° C. until an outlet air temperature of 45° C. was achieved. Spraying of the 14% polysorbate 80 and 0.3% guar gum solution was then initiated at a spray rate of 850 g/minute with an atomizing air pressure of 25-30 psi. Once all the solution was sprayed onto the powder bed the bed was dried until the moisture content (LOD) of the granules was less than 2.5%. The dried granules were passed through a Quadro® Co-mil® Model 197S cone mill fitted with a 0.032 inch round holed screen (2A032R02528) with 0.175 inch spacer at approximately 1000 rpm. The intent of the placebo granules is to use it as a platform for all pediatric suspension dosage form.

It is worth noting that the individual components of the placebo granules can be added directly to the pazopanib powder blend for reconstitution formulation without changes to the product quality, processability, and physical stability of the powder for reconstitution. In this case, the preparation of the platform granules can be avoided.

Sieve analysis was performed and bulk/tapped density profiles established. Sieve analysis was performed using a Retsch sieve shaker, Model AS200 Digit. Approximately 55 g of the dried platform placebo granules was placed on the top of a nest of tared sieves of 20, 40, 60, 80, 100, 200, 270, and 325 meshes. Shaking was done for 5 minutes at an amplitude setting of 60 with the pulse on. This sieve analysis revealed little batch to batch variation in particle size of the platform granules. The granules were also characterized for Bulk Density (BD) and Tapped Density (TD) using a VanKel Tap Density Meter. BD and TD of the granules were measured by adding a weighed amount of granules into a 100 ml graduated cylinder and measuring the volume initially and after 100, 200, 300 and 500 taps respectively. BD and TD showed minimal variation between batches. Carr indices were less than 12 which are indicative of good flowability of the platform placebo granules.

(ii) Pazopanib Powder Blend for Reconstitution Formulation (Batch Size 10,000 Grams)

A simple four step secondary manufacturing process was developed for the powder for reconstitution to a suspension formulation which includes Blending, Milling, Blending and Filling. The first process step was blending, during this phase of the process all excipients were screened through a 30 mesh screen and 5-[[4-[(2,3-dimethyl-2H-indazol-6-yl)

methylamino]-2-pyrimidinyl]amino]-2-methylbenzenesulfonamide hydrochloride was screened through a 4 mesh screen and transferred to a Servolift 50 L bin blender. The materials were blended for 15 minutes at 15+/−2 rpm. The second process step was milling, this unit operation was used to delump and narrow the particle size distribution of the blend using a Quadro® Co-mil® assembled with a 0.032 inch round holed screen (2A032R02528) at 1000 rpm. In the third step, the milled material was placed back into the Bin Blender and blended at 15+/−2 rpm for 25 minutes to achieve uniform distribution of the drug substance and excipients.

The process of Example 1 resulted in a composition having the following composition shown in Table 3.

The target amount 13.87 grams is designed to be reconstituted with 90 mL of purified water to achieve a final concentration of pazopanib of 50 mg/mL.

TABLE 3

| COMPOSITION & SPECIFICATION | UNIT FORMULA (g/bottle) (w/w %) | FUNCTION |
| --- | --- | --- |
| pazopanib hydrochloride, micronized | 5.420 (39.0%) | Active substance |
| Grinsted Guar Gum 5000 | 0.681 4.9% | Thickening Agent |
| Polyvinylpyrrolidone (PVP) | 1.000 7.2% | Suspending Agent/ Viscosity Modifier |
| Polysorbate 80 | 0.091 0.7% | Surfactant |
| Citric acid monohydrate | 0.650 4.7% | Buffer |
| Sodium Phosphate, Dibasic, Anydrous | 0.550 4.0% | Buffer |
| Methylparaben, Powder | 0.200 1.4% | Antimicrobial Preservative |
| Colloidal Silicon Dioxide | 0.070 0.5% | Anti-adherent |
| Sucralose powder | 1.400 10.0% | Sweetener |
| Mannitol Pearlitol 100SD | 3.498 25.2% | Process Aid/ Sweetener |
| Lemon Flavor | 0.310 2.2% | Flavor |
| TOTAL RECONSTITUTION VEHICLE | 13.870 | |
| Purified Water | 90 mL | Vehicle |

Example 2

Comparative Formulations

Table 4 depicts a qualitatively similar formulation to the exemplary formulation, Example 1. Both formulations were manufactured using the same unit operations and processing parameters. The main differences in the comparative formulation are that sodium phosphate was replaced with trisodium citrate and the quantities of sucralose and mannitol were slightly reduced. At long term storage conditions of 25° C./60% RH or room temperature the physical stability of the comparative suspension monitored by XRPD indicated a mixture of forms were detected at day 7 compared with the exemplary formulation (Table 3) that was stability up to 34 days. It was determined that the use of citric acid and trisodium citrate buffer system speed the conversion to the pazopanib citrate salt. It is believed that this is driven by the smaller buffering capacity of citric acid and trisodium citrate buffer.

The process of Example 2 resulted in a composition having the following composition shown in Table 4.

TABLE 4

| COMPOSITION & SPECIFICATION | UNIT FORMULA (g/bottle) (w/w %) | FUNCTION |
| --- | --- | --- |
| Pazopanib hydrochloride, Micronized | 5.420 (44.28%) | Active substance |
| Grinsted Guar Gum 5000 | 0.681 5.56% | Thickening Agent |
| Polyvinylpyrrolidone (PVP) | 1.000 8.17% | Suspending Agent/ Viscosity Modifier |
| Polysorbate 80 | 0.091 0.74% | Surfactant |
| Citric acid monohydrate | 0.660 5.39% | Buffer |
| Trisodium Citrate Dihydrate | 0.560 4.58% | Buffer |
| Methylparaben, Powder | 0.200 1.63% | Antimicrobial Preservative |
| Colloidal Silicon Dioxide | 0.070 0.57% | Anti-adherent |
| Sucralose powder | 1.100 8.99% | Sweetener |
| Mannitol Pearlitol 100SD | 2.148 17.55% | Process Aid/ Sweetener |
| Lemon Flavor | 0.310 2.53% | Flavor |
| TOTAL RECONSTITUTION VEHICLE | 12.240 | |
| Purified Water | 90 mL | Vehicle |

Example 3

Comparative Formulations

Table 5 depicts a qualitatively similar formulation to the exemplary formulation, Example 1. In this formulation the individual excipients and drug substance are blended following steps ii "Pazopanib powder blend for reconstitution formulation". The main differences in the comparative formulation are that PVP is replaced with HPMC and Polysorbate 80 is removed from the formulation.

The process of Example 3 resulted in a composition having the following composition shown in Table 5.

TABLE 5

| COMPOSITION & SPECIFICATION | UNIT FORMULA (g/bottle) (w/w %) | FUNCTION |
| --- | --- | --- |
| Pazopanib hydrochloride, Micronized | 5.420 (41.60%) | Active substance |
| Grinsted Guar Gum 5000 | 0.680 5.22% | Thickening Agent |
| Hypromellose, HPMC | 0.200 1.53% | Suspending Agent |
| Citric acid monohydrate | 0.650 4.99% | Buffer |
| Sodium Phosphate Dibasic, Anhydrous | 0.550 4.22% | Buffer |
| Methylparaben | 0.2500 1.92% | Antimicrobial Preservative |
| Colloidal Silicon Dioxide | 0.070 0.54% | Anti-adherent |
| Sucralose powder | 1.400 10.74% | Sweetener |

TABLE 5-continued

| COMPOSITION & SPECIFICATION | UNIT FORMULA (g/bottle) (w/w %) | FUNCTION |
|---|---|---|
| Manitol Pearlitol 100SD | 3.500 26.86% | Process Aid/ Sweetener |
| Lemon Flavor | 0.310 2.38% | Flavor |
| TOTAL RECONSTITUTION VEHICLE | 13.03 | |
| Purified Water | 90 mL | Vehicle |

What is claimed is:

1. Direct blend powder for use in a pharmaceutical composition, comprising
   i) micronized 5-[[4-[(2,3-dimethyl-2H-indazol-6-yl)methylamino]-2-pyrimidinyl]amino]-2-methylbenzenesulfonamide hydrochloride, wherein said micronized 5-[[4-[(2,3-dimethyl-2H-indazol-6-yl)methylamino]-2-pyrimidinyl]amino]-2-methylbenzenesulfonamide hydrochloride has a particle size distribution such that more than 90% of the particles are between 0.61 and 10.0 microns;
   ii) 3.0 to 12.0 w/w % guar gum as a thickening agent,
   iii) 0.5 to 4.0 w/w % hypromellose as a suspending agent,
   iv) buffer,
   v) preservative,
   vi) anti-adherent or glidant,
   vii) sweetener, and
   viii) flavor.

2. The direct blend powder according to claim 1 wherein said guar gum is present as from 3.0 w/w % to w/w 8.0%.

3. An oral suspension comprising
   a) a direct blend powder comprising
      i) 35.0 to 50.0 w/w % 5-[[4-[(2,3-dimethyl-2H-indazol-6-yl)methylamino]-2-pyrimidinyl]amino]-2-methylbenzenesulfonamide hydrochloride,
      ii) 3.0 to 12.0 w/w % guar gum as a thickening agent,
      iii) 0.5 to 4.0 w/w % hypromellose as a suspending agent,
      iv) buffer,
      v) preservative,
      vi) anti-adherent,
      vii) sweetener,
      viii) flavor, and
   b) purified water.

4. The oral suspension according to claim 3 wherein said guar gum is present as from 3.0 w/w % to 8.0 w/w %.

5. The oral suspension according to claim 3 wherein said 5-[[4-[(2,3-dimethyl-2H-indazol-6-yl)methylamino]-2-pyrimidinyl]amino]-2-methylbenzenesulfonamide hydrochloride is micronized.

6. The oral suspension according to claim 5 wherein said micronized 5-[[4-[(2,3-dimethyl-2H-indazol-6-yl)methylamino]-2-pyrimidinyl]amino]-2-methylbenzenesulfonamide hydrochloride has a particle size distribution such that more than 90% of the particles are between 0.61 and 10.0 microns.

* * * * *